United States Patent [19]

Schlegal

[11] Patent Number: 5,376,542
[45] Date of Patent: Dec. 27, 1994

[54] METHOD FOR PRODUCING IMMORTALIZED CELL LINES USING HUMAN PAPILLUMA VIRUS GENES

[75] Inventor: Richard Schlegal, Rockville, Md.

[73] Assignee: Georgetown University, Washington, D.C.

[21] Appl. No.: 874,397

[22] Filed: Apr. 27, 1992

[51] Int. Cl.$^5$ .................. C12N 15/63; C12N 5/10; A61K 48/00
[52] U.S. Cl. ...................... 435/172.2; 435/172.3; 435/240.1; 435/240.2; 935/62; 935/71; 935/93
[58] Field of Search ............... 435/172.3, 172.2, 240.2, 435/240.1, 320.1; 935/62, 70, 71, 55–57, 24, 32, 93; 424/93 B

[56] References Cited

PUBLICATIONS

Neoplastic Transformation in Human Cell Culture, copyright 1991 by The Humana Press Inc., Papers from a workshop held at Georgetown University Medical Center, Washington, D.C. on Apr. 25–26, 1991.

Abstracts of papers presented at the 1991 Papillomavirus Workshop Jul. 20–26, 1991 in Seattle, Washington on the campus of the University of Washington.

Inverse Relationship between Human Papillomavirus Type 16 Early Gene Expression and Cell Differentiation in Nude Mouse Epithelial Cysts and Tumors Induced by HPV–Positive Human Cell Lines, vol. 65, No. 2, Journal of Virology, Feb. 1991, pp. 796–804.

Notes on the E6 and E7 Genes of the Human Papillomavirus Type 16 Together Are Necessary and Sufficient for Transformation of Primary Human Keratinocytes, vol. 63, No. 10, Journal of Virology, Oct. 1989, pp. 4417–4421.

Short Report on the E6 and E7 genes of HPV–18 are sufficient for inducing two–stage in vitro transformation of human keratinocytes, The Macmillan Press Ltd. 1989, Oncogene (1989), 4, 1529–1532.

Differences in Transformation Activity between HPV–18 and HPV–16 Map to the Viral LCR–E6–E7 Region, Virology 181, 374–377 (1991) by Lusia Lina Villa and Richard Schlegel.

Immortalization and Altered Differentiation of Human Keratinocytes in Vitro by the E6 and E7 Open Reading Frames of Human Papillomavirus Type 18, vol. 64, No. 2, Journal of Virology, Feb. 1990, pp. 519–526.

Altered Expression of Proliferation and Differentiation Markers in HJuman Papillomavirus 16 and 18 Immortalized Epithelial Cells Grown in Organotypic Culture, American Journal of Pathology, vol. 140, No. 1, Jan. 1992.

The E7 Gene of Human Papillomavirus Type 16 is Sufficient for Immortalization of Human Epithelial Cells, Journal of Virology, Jan. 1991, pp. 473–478, vol. 65, No. 1.

Immortalization of Normal Human Bronchial Epithelial Cells by Human Papillomaviruses 16 or 18, Cancer Research 51, 5370–5377, Oct. 1, 1991.

Loss of p53 Protein in Human Papillomavirus Type 16 E6–Immortalized Human Mammary Epithelial Cells, vol. 65, No. 12, Journal of Virology, Dec. 1991, pp. 6671–6676.

Human Cervical and Foreskin Epithelial Cells Immortalized by Human Papillomavirus DNAs Exhibit Dysplastic Differentiation in Vivo, Cancer Research 50, 3709–3715, Jun. 15, 1990.

In Vitro Biological Activities of the E6 and E7 Genes Vary among Human Papillomaviruses of Different Oncogenic Potential, Journal of Virology, Jan. 1991, pp. 292–298, vol. 65, No. 1.

Epithelial Cells Immortalized by Human Papillomaviruses Have Premalignant Characteristics in Organotypic Culture, American Journal of Pathology, vol. 138, No. 3, Mar. 1991, pp. 673–685.

*Primary Examiner*—Jacqueline Stone
*Attorney, Agent, or Firm*—Burns, Doane, Swecker & Mathis

[57] ABSTRACT

A process of immortalizing cells with isolated HPV–16, 18, 31, 33 or 35 E6 and E7 genes or the E7 gene alone to produce non-tumorigenic immortalized cell lines which retain the differentiated phenotypic characteristics of the parent cells.

4 Claims, 1 Drawing Sheet

METHOD FOR PRODUCING IMMORTALIZED CELL LINES USING HUMAN PAPILLUMA VIRUS GENES

BACKGROUND OF THE INVENTION

1. Field of the Invention

The present invention is directed to the immortalizing E6 and E7 genes of human papilloma viruses, such as virus types 16, 18, 31, 33 and 35 and transfection of these genes into target cells. In vivo expression of E6/E7 genes immortalizes the target cell which retains its phenotypic characteristics.

2. Discussion of the Background

More than 50 different types of human papillomariruses (HPVs) have now been isolated from a variety of squamous epithelial lesions, and approximately 18 of them have been associated with anogenital tract lesions. Some of these, such as HPV type 6 (HPV-5) and HPV-11, are generally associated with benign proliferative lesions, including condyloma acuminata, which only infrequently progress to cancers. Others, such as HPV-16, HPV-18, HPV-31, HPV-33, and HPV-35, are associated with genital tract lesions, which are at risk for malignant progression, and with genital tract cancers (1).

HPV-16 or HPV-18 DNA has been found integrated in a high percentage of cervical carcinomas and in cell lines derived from these cancers (2, 3, 4). This is in contrast with the premalignant dysplastic lesions associated with HPV-16 and HPV-18, in which the viral DNA is usually found in an extrachromosomal state (5). In several cases in which the number of integrated viral genomes was low enough to permit a detailed analysis, the integration pattern revealed remarkable specificity with respect to the circular viral genome. Integration occurs in the E1-E2 region (6, 7, 8), disrupting the E2 viral transcriptional regulatory circuitry. The E2 open reading frame (ORF), as originally demonstrated with the bovine papillomavirus type 1, encodes both positive- and negative-acting transcriptional regulatory factors (9, 10). For HPV-16 and HPV-18, E2 appears to act principally as a repressor of the promoter from which the E6 and E7 genes are transcribed (11, 12). The HPV genomes in cervical carcinomas and in derived cell lines are transcriptionally active, and the patterns of viral mRNA species are specific, with regular expression of the E6 and E7ORFs (6, 13, 14).

The E7ORF of HPV-16 encodes a 21-kilodalton phosphoprotein (14), and the E7 genes of HPV-16 and HPV-18 are sufficient for focus formation of established rodent fibroblasts such as NIH 3T3 cells (15, 16, 17, 18, 19). The E7 protein is functionally and structurally related to the adenovirus E1A proteins (AdE1A); it can transactivate the AdE2 promoter and can cooperate with an activated ras oncogene to transform primary rat cells (16, 20). The amino-terminal 38 amino acids of E7 are strikingly similar to portions of conserved domain 1 (amino acids 37 to 49) and domain 2 (amino acids 116 to 137) of the AdE1A proteins (16) as well as to portions of the large tumor antigens (T) of papovaviruses. The AdE1A, simian virus 40 (SV40) T, and HPV-16 E7 proteins form specific complexes with the product of the retinoblastoma tumor suppressor gene (p105-RB) (21, 22, 23), and complex formation with p105-RB is mediated through these conserved sequences for AdE1A and SV40 T (21, 22) as well as for HPV-16 E7. The transforming potential of the E6 gene has been less well defined. In NIH 3T3 fibroblasts, it may contribute to characteristics of the transformed phenotype such as anchorage independence (25) or tumorigenicity in nude mice (26). In human cells, E6 appears to cooperate with the E7 oncoprotein in mediating-cellular immortalization. Recently, it has been demonstrated that E6 binds to, and mediates the degradation of, the cellular tumor suppressor protein p53. It has been shown recently that both the E6 and E7ORFs are necessary for the extension of the life span of human diploid fibroblasts (34). Mutation studies of the early HPV-16 genes that directly participate in the in vitro transformation of primary human keratinocytes has shown that both the full-length E6 and E7 genes are required for induction of keratinocyte immortalization and resistance to terminal differentiation (35). Keratinocyte transformation with HPV-18 DNA requires only the HPV-18 regulatory region and the E6/E7 genes which induce two progressive steps in cellular transformation (36).

A quantitative keratinocyte assay has been used to demonstrate that the HPV genes can alter the response of human keratinocytes to inducers of terminal differentiation. HPV-16 and HPV-18 DNA can immortalize human keratinocytes in vitro. These immortalized cell lines exhibit altered characteristics of cellular proliferation and differentiation but are not tumorigenic in nude mice. They contain integrated copies of HPV DNA and express viral mRNAs and proteins (27, 28, 29, 30, 31, 32). While the above in-vitro assays rely on the growth of keratinocytes on plastic substrate and can be criticized for its lack of physiologic relevance, other in vitro assays which more closely mimic the in vivo conditions for squamous cell growth have demonstrated similar results. Thus, when human keratinocytes are grown by the collagen raft cell culture technique, they display an enhanced cellular differentiation and stratification which is very similar to, but not identical with, that observed of keratinocytes in vitro. This technique has been successfully applied to the study of HPV gene effects on cellular differentiation and several laboratories have demonstrated that the E6/E7 genes produce altered cellular differentiation reminiscent to that observed in cervical dysplasia (33). Thus, all experimental data to date suggests that the expression of the E6/E7 genes results in a poorly differentiated phenotype when assayed in vitro.

(In a recent study, HPV-16 immortalized human keratinocytes were subcutaneously injected into nude mice. Although the immortalized cells retain the ability for differentiation after injection, the injected cells were immunoisolated to form encapsulated cysts).

The study of normal cell growth and differentiation would be greatly augmented by the development of an efficient method for obtaining human immortalized cell lines which would retain their ability to differentiate and respond to external regulatory signals. One critical research area which would greatly benefit from such an approach would be the study of cystic fibrosis (CF). Not only would CF cell lines permit the analysis of the altered ion permeability properties of these cells and their alteration by pharmacologic agents, but they would also serve as a substrate for future gene therapy experiments. In an attempt to generate such cell lines, the SV40 large T antigen has been used to immortalize CF cells. Unfortunately, the derived cell lines lose many of their differentiated properties and are inadequate for biochemical, physiological, and molecular analysis.

A need continues to exist for a means of immortalizing human cells in a non-tumorigenic manner such that the immortalized cells retain their differentiated phenotypic properties. A broadly applicable means for producing non-tumorigenic immortalized cell lines would facilitate research on gene products of particular cells, provide cell lines capable of producing large quantities of gene products without the need to replace senescent cell lines; provide immortalized cell lines for use in direct gene therapy applications and also provide a means of immortalizing cell lines containing exogenous genes or genes which have been subjected to site-specific mutation to correct abnormalities in gene expression.

SUMMARY OF THE INVENTION

One object of the present invention is a method of immortalizing cells by a process in which the immortalized cells retain their differentiated phenotypic properties and characteristics in vivo and are non-tumorigenic.

Another object of the invention is a process for immortalizing cells which is widely applicable to a broad variety of different cell types.

A further object of the invention is a method of gene therapy in which cells from a patient are removed from the patient and immortalized to produce non-tumorigenic immortalized cells retaining the differentiated phenotypic characteristics of the original parent cells, and then reintroducing the immortalized cells into the patient as a therapeutic treatment.

Still a further object of the invention is a method of gene therapy in which cells having a defective gene are obtained from a patient. The defective gene can then repaired by site-specific mutation or be replaced by an exogenous gene capable of expressing the desired gene product. This genetically altered host cell can then immortalized to produce a non-tumorigenic immortalized cell line expressing the desired gene product.

These and other objects of the invention which will become apparent from the following specification have been achieved by the present process of immortalizing cells with isolated HPV-16, 18, 31, 33 or 35 E6 and E7 genes or the E7 gene alone to produce non-tumorigenic immortalized cell lines which retain the differentiated phenotypic characteristics of the parent cells.

DETAILED DESCRIPTION OF THE PREFERRED EMBODIMENTS

Figure 1:
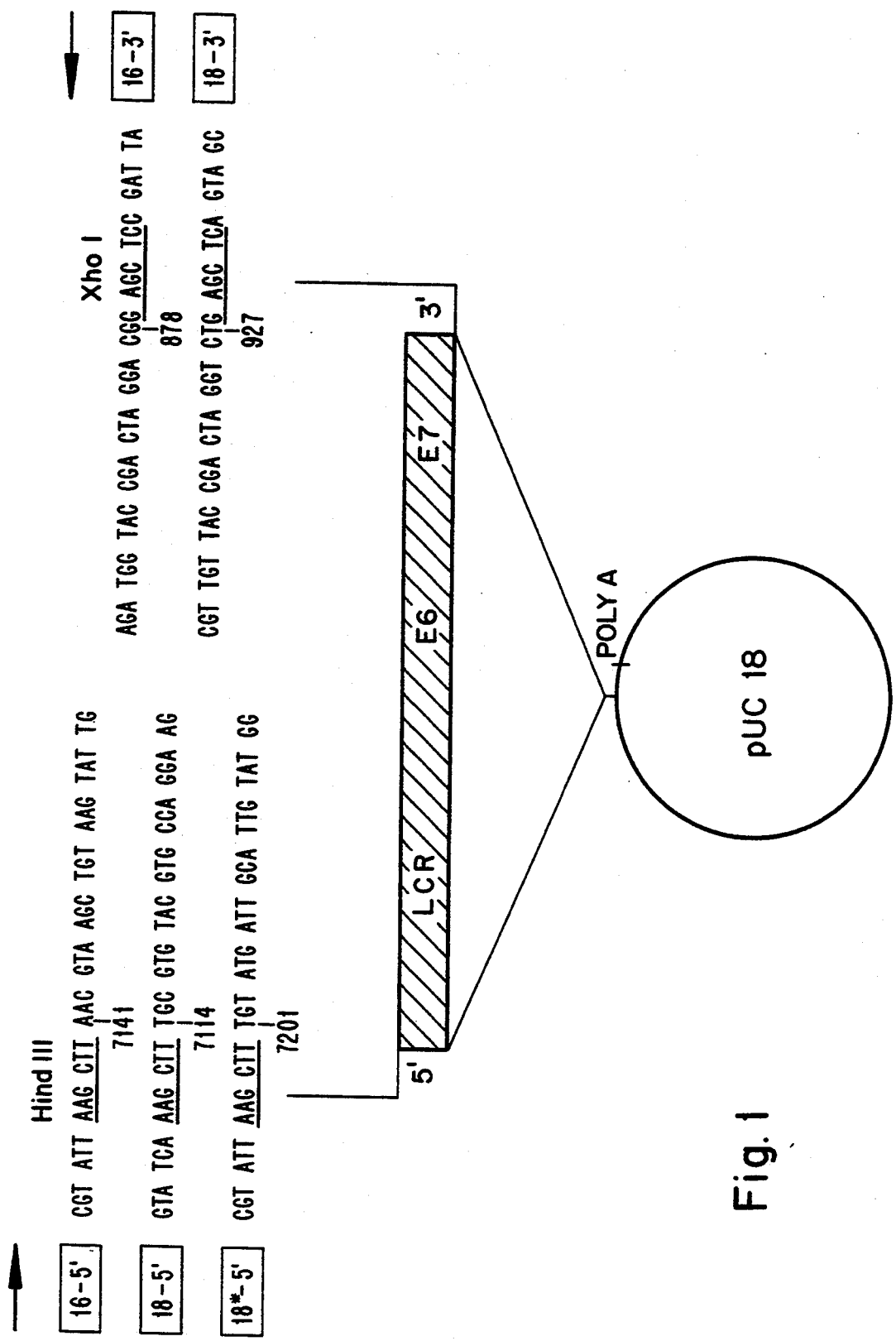
FIG. 1 diagrammatically shows the amplification and cloning of the LCR-E6-E7 region of HPV-16 and HPV-18 from human tumors.

HPV-16, 18, 31, 33 and 35 DNA has been shown to immortalize human keratinocytes in vitro. However, continued growth of these non-tumorigenic cell lines in vitro results in altered or dysplastic cellular proliferation and differentiation characteristics. That is, keratinocytes immmortalized with HPV E6/E7 genes and grown in vitro lose some or many of the differentiated phenotypic characteristics of the parent keratinocytes. Non-tumorigenic immortalized cells are not suitable for gene therapy applications due to the loss of differentiated phenotypic characteristics.

Surprisingly, it has now been discovered that epithelial and non-epithelial cells which have been immortalized with HPV-16, 18, 31, 33 or 35 E6 and E7 genes or the E7 gene alone, retain the differentiated phenotypic characteristics of the parent epithelial and non-epithelial cells when grown in vivo in the host animal after immortalization. The loss of phenotypic characteristics which is seen when the immortalized cells are grown in vitro is prevented when these cells are grown in vivo in the host animal. Immortalized host cells which retain the phenotypic characteristics of the parent cells are not immunogenic to the host immune system and are therefore useful for gene therapy.

By "retain the phenotypic differentiated characteristics" of parent cells used herein, is meant that the phenotypic characteristics of stable immortalized cells are indistinguishable from parent cells, when the immortalized cells are grown in vivo. In vivo growth can be in a nude mouse or in the host mammal or human patient. The phenotypic characteristics can be easily determined by conventional methods such as histologic examination using standard strains. Where the immortalized cells express a gene product, the cell "retains the phenotypic differentiated characteristics" of the parent cell when it expesses the gene product in vivo or in vitro. By "stable, immortalized cells" it is meant that the immortalized cells which are administered into the host animal will proceed to grow and differentiate normally and will not undergo induced terminal differentiation and death subsequent to immune rejection.

Human tumors containing HPV E6/E7 genes are widely available as described above. A scheme for the isolation of HPV E6/E7 genes from human tumors is illustrated in FIG. 1. LCR is the HPV viral promoter. In brief, cellular DNA from carcinomas of the uterine cervix, vulva and penis from patients is purified using standard techniques (Sambrook et al, *Molecular Cloning: A Laboratory Manual*, second edition. Cold Spring Harbor Laboratory, Cold Spring Harbor, N.Y., 1989). The HPV DNA present in each sample is typed by Southern hybridization and only those samples containing HPV-16 or HPV-18 DNA are further utilized.

PCR techniques for amplifying a selected DNA sequence are well known in the art. See Erlich, H. A., *PCR Technology—Principles and Applications for DNA Amplification*, Stockton Press, New York, N.Y. 1989. The PCR techniques described in this reference can be readily used to amplify the HPV E6 and E7 genes are were then inserted into a cloning vector using standard recombinant DNA technology.

Purified tumor DNA is amplified by polymerized chain reaction (PCR) using the designated oligonucleotides corresponding to the 5' end of the LCR promoter (defined as the terminus of the L10FR) and that 3' end of the E7 gene (immediately following the termination codon). In the case of HPV-18, an additional oligonucleotide is used to amplify the LCR from an internal position (bp 7201). For each of the oligonucleotides (see FIG. 1), a non-homologous 5' terminus encoding either a restriction site (HindIII or XhoI, for example) is included to facilitate the unidirectional cloning of the amplified fragment into a mutable plasmid. (Baker et al, in *Recombinant Systems in Protein Expression*, pages 75–86, Elsevier, Amsterdam/New York, 1990). The orientation of the amplified HPV LCR E6-E7 region can be verified by direct sequencing.

The plasmids constructed as described above can be evaluated in a quantitative transformation assay and compared with full-length genomes of HPV-16 and HPV-18 to verify the presence of the HPV genes in the plasmid. HPV-18 has a transformation efficiency approximately 10 fold greater than HPV-16. The relative transforming activity of HPV-18 to HPV-16 is maintained in a subgenomic fragment containing only the LCR-E6-E7 region, indicating that other viral genes are not responsible for this difference in activity.

The HPV E6-E7 genes can be incorporated into any standard cloning vector. The term "vector" is well understood in the art and is synonymous with the often-used phrase "cloning vehicle". A suitable vector is a non-chromosomal double-stranded DNA comprising an intact replicon such that the vector is replicated when placed within a unicellular organism.

Viral vectors include retroviruses, adenoviruses, herpes virus, papovirus, etc. Other suitable vectors include plasmids. Plasmids and retroviruses and preferred vectors.

In FIG. 1, pUC18 was constructed and contained the natural HPV LCR viral promoter. This promoter is suitable for expression of the E6-E7 genes in a wide variety of cells including both epithelial and non-epithelial cells. However, the LCR promoter is not specifically required for transcription and expression of the E6-E7 genes. optionally, one may replace the LCR promoter with other known promoters to improve the efficiency of transcription and expression in particular cells.

Many promoters optimally active in specific cell types are known in the art. For example, immortalization of the following cell types can be improved by using the specific known promoter identified: muscle cells/myosin promoter, fibroblasts/actin promoter, pancreas cells/insulin promoter, bowel/lactase or sucrase, prostate cells/acid phosphatase promoter, liver cells/albumin promoter and lung cells/cystic fibrosis (CF) gene promoter.

The promoter DNA can be amplified using PCR technology while concurrently providing restriction sites at the 5' and 3' ends of the promoter DNA. The amplified promoter DNA can then be inserted into a cloning vehicle (for example pUC18) using conventional endonucleases and known recombinant DNA technology. Cloning vectors containing the desired promoter upstream of the 5' end of the E6 or E7 genes are constructed in this manner.

Immortalization of cells with E6-E7 genes proceeds with high efficiency. Additionally, it is possible to immortalize cells using only the HPV E7 gene. Cloning vectors containing an appropriate promoter and the E7 gene are constructed using PCR technology in a manner analogous to the preparation of vectors containing E6/E7 genes described above. For example, recombinant retrovirus plasmids containing HPV genes E6 and E7 (Galloway et al, *J. Virol.* 65:473-478. 1991) are digested with exonuclease enzymes to remove the upstream E6 gene portion leaving an intact E7 gene. The E7 gene is then amplified and provided with appropriate restriction sites using PCR technology in the manner described above. The E7 gene is then inserted into an appropriate cloning vector using recombinant DNA technology after selecting and incorporating the desired promoter DNA sequence as described above. In this manner, a cloning vehicle containing the promoter-E7 gene is constructed.

Cloning vectors containing HPV-16, 18, 31, 33 or 35 E6/E7 genes are transfected into host cells using known transfection processes. For epithelial cells, suitable transfection processes are lipofection, electroporation and retrovirus infection. For non-epithelial cells, use of calcium phosphate according to known procedure of van der Eb is sufficient to achieve transfection. Retrovirus transfection is the preferred mode of transfection for both epithelial and non-epithelial cells. Lipofection is a preferred alternative method for transfection of epithelial cells. Electroporation according to the method of Schlegel et al (30) is a preferred second alternative for transfection of lymphocytes. Calcium phosphate transfection according to the method of van der Eb is a preferred second alternative for transfection of mesenchymal cells and fibroblasts.

When transfecting cells with electroporation, the desired cells are isolated and cultured in suitable media. Electroporation is conducted using commercially available equipment according to known methods using optimum voltage and current settings. The voltage and current settings can be readily determined by one having ordinary skill in the art in consultation with the manufacturers manual accompanying conventional electroporator devices. The isolated cells are electroporated with 1-20 micrograms of linearized HPV or plasmid DNA containing the promoter and E6/E7 genes. Transfected cells are then replated into growth medium and analyzed for microcolony formation after several days. The efficiency of immortalization following electroporation in approximately 5-20 transformants/$10^6$ cells electroporated.

Transfection of cells using lipofection is conducted according to standard lipofection procedures. See Felgner et al. 1987. *Proc. Natl. Acad. Sci. (USA).* 84:7413-7417. In general, liposome-mediated DNA transfection is accomplished by exposing 1-20 micrograms of plasmid DNA and commercially available liposomes (Bethesda Research Laboratories) in culture medium. The transfected cells are then repeatedly passaged in culture medium and the desired clones are isolated. The efficiency of immortalization by lipofection in approximately 50-100/$10^6$ cells lipofected.

Retrovirus infection is also accomplished using previously described procedures. See for example Miller et al. *J. Virol.* 62:4337-4345 and Halbert et al. *J. Virol.* 65:473-378. 1991. In general, plasmid DNA is transfected into a desired packaging cell line such as Psi-2 or other cell lines, using standard calcium phosphate precipitation. Viruses produced from the Psi-2 cells or equivalent cells are then used to infect an amphotropic packaging cell line, for example PA317. Viruses produced by the amphotropic packaging cell line are used to infect the desired host parent cells of the present invention. Immortalization efficacy with retroviruses approximates >1000 transformants/$10^6$ cells infected.

After transfection, the desired clones are selected by culturing in optimal media and repeated passaging. Generally, 10-20 passages are required to eliminate spurious cells and obtain pure clonal cells. Optimal media are selected according to the type of parent cell which is immortalized. For lymphocytes, RPMI media is preferred; for fibroblasts, DMEM media is preferred; and for epithelial cells, a serum-free medium such as keratinocyte growth medium (KGM) or SFM (Gibco Company) is preferred.

Selected colonies are then tested to verify the presence of HPV DNA and the expression of E6/E7 genes. Verification is confirmed by standard Southern hybridization techniques and immunoprecipitation to determine the presence of expressed E6 and E7 proteins (36)

The present invention provides a means for immortalizing any cell type to produce cells which retain the differentiated phenotypic characteristics of the parent cells. Epithelial cells are particular preferred host cells for immortalization using the method of the present invention.

Specific epithelial cells which can be immortalized using the present method include those lining the respiratory, gastrointestinal, genitourinary and nervous systems. Examples of such epithelial cells include those of the oral and nasal mucosa, larynx, trachea, lung, esophagus, stomach, duodenum, jejumin, ileum, and colon. Other epithelial cells which can be immortalized include liver, pancreas, kidney, bladder, adrenal and reproductive organ epithelial cells, such as cells obtained from the ovary, uterus (endometrium), testis and prostate. Skin cells can also be immortalized, in particular hair follicle cells and dermal papillae which are necessary for hair follicle development.

In addition to epithelial cells, non-epithelial cells such as endothelial cells, fibroblasts, muscle cells, bone cells, cartilage cells and brain tissue cells (neurons, glial cells, etc.) can also be immortalized using the method of the present invention. Further, hematopoietic cells such as red blood cell progenitor cells, white blood cell progenitor cells and megakariocytes can all be immortalized. These immortalized hematopoietic cells can be reintroduced into a host mammal during gene therapy to treat blood system diseases such as aplastic anemia, leukemia and lymphomas.

Gene therapy refers to the transfer and stable insertion of new genetic information into cells for the therapeutic treatment of diseases or disorders. The foreign gene is transferred into a cell that proliferates to spread the new gene throughout the cell population. Known methods of gene transfer include microinjection, electroporation, liposomes, chromosome transfer, and transfection techniques as well as calcium-precipitation transfection techniques as disclosed above.

Disorders that can be treated by infusion of immortalized cells include but are not limited to three broad categories. First are diseases resulting from a failure or dysfunction of normal blood cell production and maturation (i.e., aplastic anemia), as well as neoplastic, malignant diseases in the hematopoietic organs (e.g., leukemia and lymphomas). The second group of disorders comprises those of patients with broad spectrum of malignant solid tumors. The third group of diseases comprises a number of genetic disorders which can be corrected by infusion of immortalized cells, which prior to transplantation have been modified to contain an exogenous gene.

Numerous techniques are known in the art for the introduction of foreign genes into cells and may be used to construct the recombinant cells for purposes of gene therapy, in accordance with this embodiment of the invention. The technique used should provide for the stable transfer of the heterologous gene sequence to the stem cell, so that the heterologous gene sequence is heritable and expressible by stem cell progeny, and so that the necessary development and physiological functions of the recipient cells are not disrupted. Techniques which may be used include but are not limited to chromosome transfer (e.g., cell fusion, chromosome-mediated gene transfer, micro cell-mediated gene transfer), physical methods (e.g., transfection, spheroplast fusion, microinjection, electroporation, liposome carrier), viral vector transfer (e.g., recombinant DNA viruses, recombinant RNA viruses) etc. (described in Cline, M. J., 1985, Pharmac. Ther. 29:69–92.)

In general, for the treatment of cancer, it is contemplated that the modified cells (i.e. tumor-specific lymphocytes) release various molecules that adversely affect the tumor by interfering with its blood supply, by stimulating the immune system to reject the tumor, or by interfering with the processes of tumor growth or invasion. Of course, some substances may act upon the immune response as well as upon the blood supply of the tumor, such as IL-1α, HLA or TNF.

There is increasing evidence that a number of cancers are remarkably sensitive to extremely high doses of normally ineffective anti-neoplastic drugs. These cancers include malignant melanoma, carcinomas of the stomach, ovary, and breast, small cell carcinoma of the lung, and malignant tumors of childhood (including retinoblastoma and testicular carcinoma), as well as certain brain tumors, particularly glioblastoma.

In another specific embodiment, patients with infections by pathogenic microorganisms can be treated with recombinant immortalized cells. Such recombinant cells can contain a heterologous gene which is expressed as a product which ameliorates disease symptoms, is toxic to the pathogen without significant detriment to the host, or interferes with the pathogen's life cycle, etc. Pathogens which cause infections which may be treated with recombinant cells according to this embodiment of the invention include but are not limited to lymphotropic viruses such as Human Immunodeficiency Virus (HIV, the etiological agent of acquired immune deficiency syndrome (AIDS)) (Gallo et al., 1984, Science 224:500–503; Barre-Sinoussi, F., et al., 1983, Science 220:868; Levy, J. A., et al., 1984, Science 225:840); gram-negative bacilli such as Brucella or Listeria; the mycobacterium which cause tuberculosis, or which cause Hansen's disease (leprosy); parasites such as Plasmodium (the etiological agents of malaria), or Leishmania; and fungi (such as those that cause pneumonia and other lethal infections secondary to immunodeficiencies) (for a discussion of many of these disorders, see Harrison's Principles of Internal Medicine, 1970, 6th Edition, Wintrobe, M. M., et al., eds., McGraw-Hill, New York, pp. 798–1044).

As a particular embodiment, it is possible to construct recombinant cells that express a sequence which is "anti-sense" to the nucleic acid of a pathogen. Such a sequence, which is complementary to the pathogen's NA or DNA, can hybridize to an inactivate such RNA or DNA, inhibiting the function or expression of the nucleic acid and disrupting the pathogen's life cycle. As a particular example, recombinant cells can be used in the treatment of AIDS, a disorder which is cased by HIV, apparently by infection of T4 lymphocytes (Dagleish et al., 1984, Nature 312:767–768). Recombinant cells which express an antisense nucleic acid that is complementary to a critical region (e.g., the long-terminal repeat or polymerase sequence) of the HIV genome (Wain-Hobson et al., 1985, Cell 40:9–17) can be used for the treatment of AIDS.

In a particular interesting aspect of the present invention, lymphocytes capable of producing a specific antibody can be isolated from a patient and immortalized using the process of the present invention. The non-tumorigenic immortalized lymphocyte cells can then be injected repeatedly into the patient from the immortalized cell line to continually supplied antibodies against a target antigen. Suitable antigens include, but are not limited to, AIDS virus antigens such as gp120 and gp41 glycoproteins. Also, immortalization of tumor specific lymphocytes or infectious disease-specific lymphocytes would permit the treatment of a wide variety of neoplastic and infectious diseases which involve cellular immunity as a protective mechanism.

In addition to cancer, various non-neoplastic diseases may also be treated in accordance with the present invention. For example, hemophilia A and B may be treated with cells expressing Factors VIII and IX. Additionally, thrombotic disorders may be treated with cells expressing anti-thrombin III, Protein C or Protein S in patients with deficiencies of these proteins. Further, endocrine deficiencies may be treated with cells producing growth hormone or insulin. However, a better gene regulation is required for the insulin gene because its expression must be linked to the level of glucose in the blood.

Moreover, bone marrow failure states such as aplastic anemia, cyclic neutropenia, bone marrow hypoplasia following chemotherapy or bone marrow transplantation may be treated with cells producing G-CSF, GM-CSF, IL-3, M-CSF or c-kit ligand.

Cytokines, such as IL-1α, may be used for modulating an improved immune response to the tumor, and are useful in this dry delivery system. However, inducible promoters may be necessary for IL-1α and TGF-β.

In particular, IL-2 may be used to recruit cytotoxic T lymphocytes (CTL) and natural killer cells directed against tumor cells. T-interferon may be used for induction of class II HLA gene expression by tumor cells allowing improved recognition of tumor cells by CTLs. Also, TNF-α may be used for augmentation of the immune response to tumor cells and damage to endothelial cells supplying the tumor. It is envisioned that the genetically-modified endothelial cells will have become incorporated into the blood vessels supplying the tumor, and, thus, will be optimally situated to deliver the TNF in a locally high concentration to the tumor. This should avoid the toxicities that have been observed when TNF is administered systemically. Since the endothelial cells producing the TNF are also susceptible to the effects of the molecule, it will be necessary to place the TNF gene under the control of an inducible promoter, such as the metallothionein promoter. TNF expression would be turned on only after the endothelial cells have become incorporated into the blood supply of the tumor. Further, anemia of chronic renal failure may be treated with cells producing erythropoietin.

Although any donor gene may be used which is capable of expressing a product in and secreting it from endothelial cells, mention may be made of several non-limitative examples.

For example, cells in tumor metastasis deposits may secrete cytokines such as IL-1, IL-2, IL-4, TNFα or β, interferon or allogeneic histocompatibility (HLA) antigens to initiate an immune rejection of the tumor, or alternatively secrete agents which would interfere with further angiogenesis, such as growth factor receptor-blocking peptides.

The present invention may also be used to effect systemic secretion of agents, such as Factor VIII or to interfere with the neovascularzation of diabetic retinopathy.

In particular, the following illustrative, but non-limiting examples of donor genes may be mentioned: adenosine deaminase (ADA), Factor IX, hematopoietic growth factors (GM-CSF, G-CSF, M-CSF, erythropoietin, kit ligand, IL-3), protein C, protein S, hirudin, insulin, growth hormone and parathyroid hormone.

The transformant cells, regardless of therapeutic utility, are genetically administered in an amount of about $10^6$ to $10^{12}$ cells/kg of body weight. For higher cell numbers, it is preferably to administer the cells by slow infusion.

For example, a cell solution in sterile 5% saline or dextrose-5%-saline solution may be used having a concentration of about 106 cells/250–500 μl. Such a solution can be administered intravenously in about 30 seconds. Thus, larger numbers of cells may be conveniently administered by slow infusion. However, the cell concentration of these solutions may be varied.

Alternative to infusion, immortalized cells may be directly injected with the appropriate target organ. For example, immortalized prostate cells may be directly injected into the prostate to establish foci of genetically engineered cells. Approximately $10^6/0.25$ ml. can be injected at a single site to establish such immortalized colonies. The rejected cells will first be washed free of growth medium, suspended in sterile phosphate buffered saline, and injected with a syringe and needle. Multiple sites within an organ may be injected depending upon the necessary requirement for cell number. Additionally, it may be necessary to "wound" the normal epithelium (such as in the case of trachea or gastrointestinal tract) to permit "seeding" or grafting with the immortalized epithelial cells.

Subsequent to immortalization by the E6/E7 genes, the established cell lines can also be cultured in optimal growth medium to allow for the production of either endogenous gene products (such as growth factors, hormones, cell regulatory molecules) which are characteristic of that particular cell differentiation state or of exogenous gene products encoded by DNA transfected into the recipient immortalized host cell. The cellular gene products can consist of either external secreted proteins or internal proteins which are either soluble or matrix-associated. The in-vitro conditions and/or medium optimal cell growth have been determined for most human cell types and are characteristic for the basic cell types: epithelial and mesenchymal.

Other features of the invention will become apparent in the course of the following descriptions of exemplary embodiments which are given for illustration of the invention and are not intended to be limiting thereof.

EXAMPLES

Example 1

Amplification and cloning of the LCR-E6-E7 region of HPV-16 add HPV, 18 from human tumors. DNA was extracted and purified from primary human cervical, penile, and vulvar carcinomas. Oligonucleotides corresponding to the 5' end of the LCR (defined as the terminus of the L10RF in both HPV-16, bp 7141, and HPV-18, bp 7114) and the 3' end of the E70RF (bp 878 for HPV-16 and bp 927 for HPV-18) were used to amplify the LCR-E6-E7 region (−1.6 kb) with inclusive HindIII and XhoI cloning sites as indicated. 100 ng of tumor DNA or 0.1 ng of plasmid DNA were added to a 100-μl reaction mixture containing 10 mM Tris-HCl, pH 8.3, 50 mM KCl, 1.5 mMMgCl₂, 0.01% gelatin, 200 μM each dATP, dTTP, dCTP, and dGTP, 1 μM each primer, and 2.5 units of Taq polymerase (Perkin-Elmer Cetus), and submitted to 30 cycles of 1 min at 94°, 2 min at 55°, 5 min at 70° in a thermal cycler (Perkin-Elmer Cetus). DNA fragments of the expected size were gel purified and cloned unidirectionally into a pUC18- derived vector containing the SV40 polyadenylation signals.

Example 2

Generation of Immortalized Human Prostate Cell Line. The E6/E7 genes of HPV-18 were transfected into primary human prostate cultures (obtained from human fetal tissue, courtesy of Dr. Edward Kaighn) and have been capable of generating immortalized cell lines which differ significantly) in their phenotype from those previously generated by SV40 (Kaighn et al., Transformation of human prostate epithelial cells by strontium phosphate transfection with a plasmid containing the SV40 early region genes, Cancer Research 49:3050–3056, 1989). The primary prostate cells were grown in a serum-free medium (P48F) which contains a mixture of 8 growth factors and were infected with a retrovirus containing the HPV-18 LCR/E6/E7 region. The cells were passaged (1:2 split) until immortalized clones were detected. The cells were cuboidal, epithelial cells and differed significantly from the more fibroblastic appearance of the SV40-immortalized prostate cells.

Example 3—Cystic Fibrosis Generation of Immortalized Human Tracheal Cell Lines From Cystic Fibrosis Patients.

Primary culture. Donor tissue was obtained postmortem from a 24 year old man with cystic fibrosis who was homozygous for the phenylalanine 508 deletion in the Cystic Fibrosis Transmembrane Conductance Regulator (CFFR) gene. The trachea was cut into 2×2 cm pieces and washed with Joklik's modified essential medium (MEM) containing antibiotics, dithiothreitol (0.5 mg/ml), and DNAse 10µg/ml) at 4 degrees C for 3 hours. The tissues were then incubated in fresh supplemented MEM plus protease (Sigma Type XIV, 0.1 µg/ml) at 4 degrees for 18 hours. The epithelial cells were dislodged by gentle agitation and plated in hormone-supplemented F12 medium (F12+7X; supplements:insulin 5 µg/ml, endothelial cell growth supplement 3.7 µg/ml, epidermal growth factor 25 ng/ml, triiodothyronine $3\times10^{-8}$M, hydrocortisone $1\times10^{-6}$M, transferrin 5 µg/ml, and cholera toxin 10 ng/ml, plus ceftazidime, tobramycin, amphotericin B).

Transfection with HPV-18 E6 and E7 genes. A pUC19-based plasmid containing the HPV-18 nucleotides 6273-2440 encoding the intact E6 and E7 open reading frames, a partial E1 open reading frame, and the upstream regulatory region was transfected by lipofection as described. After a 2 hr incubation at 37, 12 ml of fresh F12+7X medium was added. On the following day the cells were fed with fresh medium.

Culture and Clonal selection. At 14-18 days post-seeding, clusters of 30-200 dividing cells of apparent clonal origin developed and were isolated using cloning cylinders. Between passages 1-4, most subclones were co-cultured with lethally irradiated NIH3T3 fibroblasts, which were removed by differential trypsinization at passage 4. Eleven clones were isolated and developed a polygonal morphology typical of air-way epithelial cells in primary culture.

Presence and expression of HPV genes in immortalized cell lines. The presence of the HPV-18 genome in selected clones was assayed using polymerase chain reaction (PCR) technology with oligonucleotide primers specific for the HPV-18 E6-E7 region. The 5' primer corresponds to HPV-18 nucleotides 105-124 and the 3' primer to nucleotides 888-907 of the HPV-18 DNA sequence. Extracts of $6\times10^3$ cells of selected clones were analyzed by PCR for 30 cycles with the following conditions: 94 C for 1 min, 50 C for 2 min, and 72 C for 3 min. An HPV-18 transformed human keratinocyte cell line (18Nco) and an SV40-transformed keratinocyte cell line were used as positive and negative controls. Agarose gel electrophoresis of PCR products demonstrated the 802 bp E6-E7 amplified product in the positive control and in all CF clones examined.

Expression of the HPV-18 E7 protein. Ten cm dishes of selected clones were metabolically labelled with $^{35}$S-cysteine for 4 hours following a 2 hr starvation in cysteine-free media. Total protein was extracted following labelling and immunoprecipitated with 20 µl of a rabbit polyclonal antibody specific for the HPV-18 E7 protein. The immunoprecipitated proteins were separated electrophoretically on a 14% acrylamide-SDS gel. Autoradiography of the gel showed the presence of the 17 kD E7 protein in both of the CF clones examined as well as the 18-Nco positive control and absent from the SV40 negative control. A combined immunoprecipitation/immunoblotting procedure was also used to detect the E7 protein. Cell extracts were immunoprecipitated as above and electrophoretically separated. The gel was then blotted onto nitrocellulose and the E7 protein was detected by Western blotting using a Protoblot (Promega) kit using a 1:100 dilution of the rabbit polyclonal antibody as primary antibody. The 17 kD E7 protein was detected in all clones examined.

Ion Transport Properties. To screen for the development of functional tight junctions, clones were passaged onto a collagen matrix support. Beginning on day following passage, transepithelial resistance (Rt) and spontaneous transepithelial potential difference (Vt) were measured daily using a WPI electrometer connected to the apical and basolateral media with calomel half-cells. Measurements were taken daily until the Vt declined or the cells senesced. Resistance was calculated from the voltage deflections induced by +/−7 µamp current pulses passed through silver- silver chloride electrodes placed in the mucosal and submucosal bathing solutions. Transepithelial resistance (RE) for the CF lines (CFTI) is similar to that observed in primary cultures of human airway epithelial cells, indicating the presence of tight junctions, while $R_t$ for SV40-transformed cells (CF/T43) is markedly decreased. Additionally, the transepithelial potential difference ($V_t$) in CF lines is −13.3 which is approximately 5-fold higher than $V_t$ in SV40-transformed airway epithelial cells.

Heterologous tracheal grafts. To assess the morphologic differentiation potential of CFT1 cells, heterologous rat tracheal grafts were prepared as described. In brief, the native epithelium was removed from excised tracheas of Fisher 344 male and female rats by freezing in liquid nitrogen, thawing at room temperature, and flushing the lumen with phosphate-buffered saline. The freeze-thaw cycle was repeated twice. A suspension of $6\times10^5$ CFT1 cells (passage 13) in 50 µl F12+7X or CF/T43 cells (passage 16) was injected in the lumen of each trachea, the ends were closed with sterile 2-0 silk suture, and the tracheas were grafted in the subcutaneous space of C57BL nude mice. After 1 to 6 wk, the grafts were removed, opened, and fixed in freshly-prepared 4% paraformaldehyde. After standard dehydration and paraffin embedding, 5 micron sections were cut and stained with Richardson's, hematoxylin and eosin (H & E) or Alcian blue-period acid Schiff (AB-PAS) stains.

Obviously, numerous modifications and variations of the present invention are possible in light of the above teachings. It is therefore to be understood that within the scope of the appended claims, the invention may be practiced otherwise than as specifically described herein.

REFERENCES (1) zur Hausen, H., and A. Schneider. 1987. In N. tSalzman and P. M. Howley (ed.), The papovaviridae, vol 2. Plenum Publishing Corp., New York.

(2) Boshart, M., L. Gissmann, H. Ikenberg, A. Kleinheinz, W. Scheurlen, and H. zur Hausen. 1984. EMBO J. 3:1151–1157.

(3) Dürst, M., L. Gissmann, H. Ikenberg, and H. zur Hausen. 1983. Proc. Natl. Acad. Sci. USA 80:3812–3815.

(4) Yee, C.L., I. Krishnan-Hewlett, C. C. Baker, R. Schlegel, and P. M. Howley. 1985. Am. J. Pathol. 119:3261–3266.

(5) Dürst, M., A. Kleinheinz, M. Hotz, and L. Gissmann. 1985. J. Gen. Virol. 66:1515–1522.

(6) Baker, C. C., W. C. Phelps, V. Lindgren, M. J. Braun, M. A. Gonda, and P. M. Howley. 1987. J. Virol. 61:962–971.

(7) Matsakura, T., T. Kanda, A. Furuno, H. Yoshikawa, T. Kawana, and K. Yoshiike. 1986. J. Virol. 58:979–982.

(8) Schwarz, E., U. K. Freese, L. Gissmann, W. Mayer, B. Roggenbuck, A. Stremlau, and H. zur Hausen. 1985. Nature (London) 314:111–114.

(9) Lambert, P. F., B. A. Spalholz, and P. M. Howley. 1987. Cell 50:69–78.

(10) Spalholz, B. A., Y. C. Yang, and P. M. Howley. 1985. Cell 42:183–191.

(11) Cripe, T. P., T. H. Haugen, J. P. Turk, F. Tabatabai, P. G. Schmid III, M. Dürst, L. Gissmann, A. Roman, and L. Turek, 1987. EMBO J. 6:3745–3753.

(12) Thierry, F., and M. Yaniv. 1987. EMBO J. 6:3391–3397.

(13) Schneider-Gädicke, A., and E. Schwarz. 1986. EMBO J. 5:2285–2292.

(14) Smotkin, D., and F. O. Wettstein. 1986. Proc. Natl. Acad. Sci. USA 83:4680–4684.

(15) Kanda, T., S. Watanabe, and K. Yoshiike. 1988. Virology 165:321–325.

(16) Phelps, W. C., C. L. Yee, K. Münger, and P. M. Howley. 1988. Cell 53:539–547.

(17) Tanaka, A., T. Noda, H. Yajima, M. Hatanaka, and Y. Ito. 1989. J. Virol. 63:1465–1469.

(18) Vousden, K. H., J. Donsinger, J. A. DiPaolo, and D. R. Lowy. 1988. Oncogene Res. 3:167–175.

(19) Watanabe, S., and K. Yoshiike, 1988. Int. J. Cancer, 41:896–900.

(20) Storey, A., D. Pim, A. Murray, K. Osborn, L. Banks, and L. Crawford. 1988. EMBO J. 7:1815–1820.

(21) DeCaprio, J. A., J. W. Ludlow, J. Figge, J. Y. Shew, C. M. Huang, W. H. Lee, E. Marsilio, E. Paucha, and D. M. Livingston. 1988. Cell 54:275–283.

(22) Dyson, N., P. M. Howley, K. Münger, and E. Harlow. 1989. Science 543:934–937.

(23) Whyte, P., K. J. Buchkovich, J. M. Horowitz, S. H. Friend, M. Raybuck, R. A. Weinberg, and E. Harlow. 1988. Nature (London) 334:124–129.

(24) Whyte, P., N. M. Williamson, and E. Harlow. 1989. Cell 56:67–75.

(25) Bedell, M. A., K. H. Jones, S. R. Grossman, and L. A. Laimins, 1989. J. Virol. 63:1247–1255.

(26) Yutsudo, J., Y. Okamoto, and A. Hakura. 1988. Virology 166:594–597.

(27) Dürst, M., R. T. Dzarlieva-Petrusevska, P. Boukamp, N. E. Fusenig, and L. Gissman. 1987. Oncogene 1:251–256.

(28) Kamur, P., and J. K. McDougall. 1988. J. Virol. 62:1917–1924.

(29) Pirisi, L., S. Yasumoto, M. Feller, J. Doninger, and J. A. DiPaolo. 1987. J. Virol. 61:1061–1066.

(30) Schegel, R., W. C. Phelps, Y. L. Zhang, and M. Barbosa. 1988. EMBO J. 7:3181–3187.

(31) Woodworth, C. D., P. E. Bowden, J. Doninger, L. Pirisi, W. Barnes, W. D. Lancaster, and J. A. DiPaolo. 1988. Cancer Res. 48:4620–4628.

(32) Woodworth, C. D., J. Doninger, and J. A. DiPaolo. 1989. J. Virol. 63:159–164.

(33) McCance, D. J., R. Kopan, E. Fuchs, and L. A. Laimins. 1988. Proc. Natl. Acad. Sci. USA 85:7169–7173.

(34) Watanabe, S., T. Kanda, and K. Yoshiike. 1989. J. Virol. 63:965–969.

(35) Munger, K., Phelps, W. C., Bubb, V., Hawley, P. M. and Schlegel, R. 1989. J. Virol. 63:4417–4421.

(36) Barbarosa, M. S. and Schlegel, R. 1989. Oncogene 4:1529–1532.

(37) Braun, L. et al. 1990. Cancer Research 507324–7332.

(38) Durst, M. et al. 1991. J. Virol. 65:796–804.

What is claimed as new and desired to be secured by Letters Patent of the United States is:

1. A method for producing non-tumorigenic immortalized cell lines which retain the phenotypic properties of the parent cells used for immortalization, which method comprises:
   (i) transfecting in vitro human epithelial cells selected from the group consisting of epithelial cells lining the oral and nasal mucosa, larynx, trachea, lung, esophagus, stomach, duodenum, jejunum, ileum, colon, liver, pancreas, kidney, bladder, adrenal, hair follicle and dermal papillae epithelial cells with a DNA vector containing a subgenomic fragment of a human papilloma virus type 16 or 16 comprising the E7 or E6 and E7 genes of said human papilloma virus type 16 or 18;
   (ii) selecting for immortalized cells which possess the phenotypic properties of the transfected epithelial cells; and
   (iii) growing said cells in explant culture comprising the parent organ.

2. The method of claim 1 wherein the transfected epithelial cells are human respiratory epithelial cells.

3. The method of claim 2 wherein the transfected human respiratory epithelial cells are human tracheal epithelial cells.

4. The method of claim 3 wherein the transfected human tracheal epithelial cells are human cystic fibrosis epithelial cells and the cells retain the ion transport properties of the parent cells used for immortalization.

* * * * *